United States Patent [19]

Usrey

[11] Plant 5,215

[45] Apr. 3, 1984

[54] *RAPHIOLEPIS INDICA* CV. MONREY

[75] Inventor: William B. Usrey, Glendora, Calif.

[73] Assignee: Monrovia Nursery Company, Azusa, Calif.

[21] Appl. No.: 408,938

[22] Filed: Aug. 17, 1982

[51] Int. Cl.[3] ..... A01H 5/03

[52] U.S. Cl. ..... Plt./54

[58] Field of Search ..... Plt./54

*Primary Examiner*—Robert E. Bagwill

[57] ABSTRACT

A new and distinct selection of *Raphiolepis indica* (L.) Lindl. Shrub (popularly known as Indian Hawthorn) which hereinafter will be referred to as *Raphiolepis indica* cultivar Monrey. *Raphiolepis indica* cv. Monrey differs from its parent, *Raphiolepis indica* cv. Enchantress, by my new selection having flowers with fewer petals which are a richer, darker pink color and a larger and looser inflorescence. Another characteristic of *Raphiolepis indica* cultivar Monrey is its more open overall growth habit.

2 Drawing Figures

DISCOVERY

This invention relates to a new and distinct selection of *Raphiolepis indica,* a member of the rose family, Rosaceae. *Raphiolepis indica* cv. Monrey was discovered as a chance seedling among *Raphiolepis indica* cv. Enchantress at Monrovia Nursery Company, 18331 E. Foothill Boulevard, Azusa, Calif. in April of 1976.

The plant to date is known to exist only within the boundaries of Monrovia Nursery and has not been offered for sale or described in any publication.

REPRODUCTION

This new selection has been strictly asexually reproduced by cuttings at Monrovia Nursery Company. The unique characteristics that set this selection apart from the parent plant and make it a new and distinct selection would be lost in sexual reproduction. Therefore, propagation is restricted to asexual reproduction and sexual reproduction is prohibited.

CHARACTERISTICS

*Raphiolepis indica* cv. Monrey differs from its parent *Raphiolepis indica* cv. Enchantress (see lower photo) in its unique dark rich pink flower color and single flowers with generally five petals. Also our selection *Raphiolepis indica cv. Monrey posesses a much broader and looser inflorescence as can be seen in the lower photo.*

The upper photograph displays the upright open growth habit of our new selection which differs from the more compact dwarf habit of the parent plant.

Our new selection, *Raphiolepis indica* cv. Monrey was deliberately selected for the attributes mentioned above and shown in the accompanying photos.

DESCRIPTION

Below is a detailed description of the new *Raphiolepis indica* cv. Monrey, the color terminology is from the British Horticultural Color Charts.

Overall size and habit: The plant at maturity (3 to 4 yrs.) has a height and width of 3 to 4 feet.

Foliage:

*Size.*—$\frac{5}{8}$ to $1\frac{3}{8}''$ wide and $1\frac{1}{2}$ to $2\frac{1}{4}''$ in length.

*Shape.*—Varying from elliptic with a cuminate tip to obovate with mucronate tip. Leaf base attenuate to cuneate.

*Color.*—Upper surfaces Spinach Green 0960. Lower surfaces Fern Green 0862/1.

*Margins.*—Serrate tending to crenate; tips on serrations absent.

*Texture.*—Coriaceous.

*Arrangement.*—Alternate.

*Pubescence.*—Adult foliage: completely glabrous Juvenile foliage: Pubescent-both surfaces velutinous.

Petioles: $\frac{1}{2}$-$\frac{1}{3}''$ in length, Fern Green 0862/1 scattered wooly pubescence.

Inflorescence:

*Size.*—Average length 4", average width $4\frac{1}{2}''$.

*Shape.*—Loose, pyramidal panicle.

*Flower color.*—Center—darker Magenta Rose 027/2. Outer portion and underneath petals — lighter Magenta Rose 027/3, fading with age to a Rhodamine Pink 527/3 then to a white (no color number listed).

*Petal shape.*—Obovate with emarginate tip.

*Petal size.*—4/16" wide by 5/16" long — average size.

*Petal number.*—Appears to be single with generally 5 petals, seldom 6.

*Peduncle.*—$\frac{1}{4}''$ *in length pubescent.*

I claim:

1. A new and distinct selection of *Raphiolepis indica* referred to as *Raphiolepis indica* cv. Monrey as substantially shown and described herein, which is characterized by a loose open habit; a larger, looser and broader inflorescence; single flowers; and rich dark pink flowers.

* * * * *

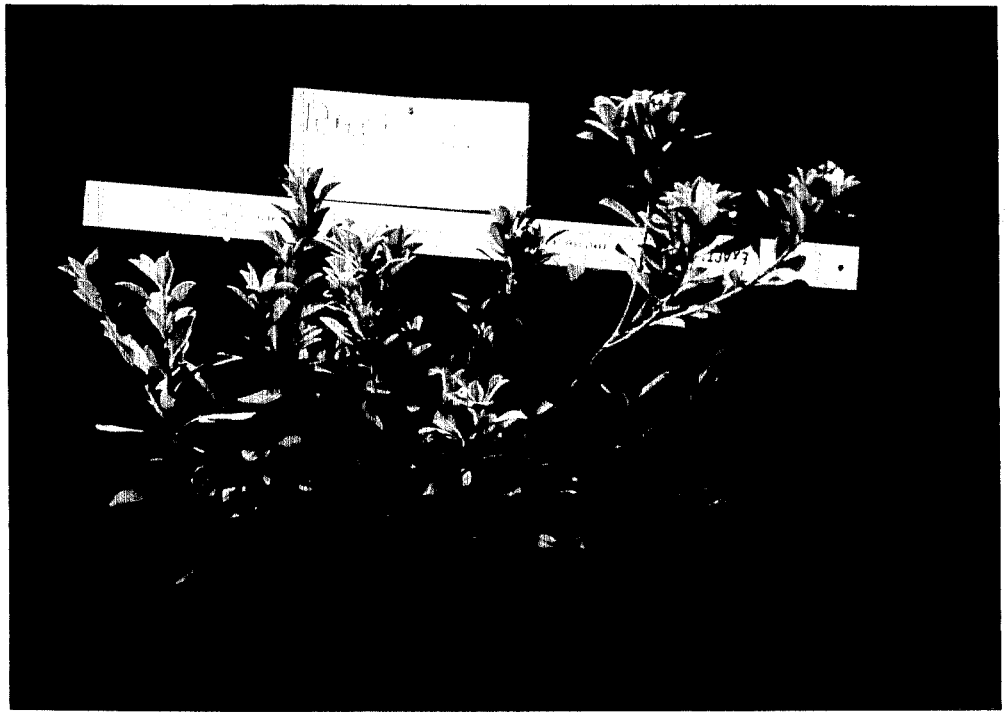
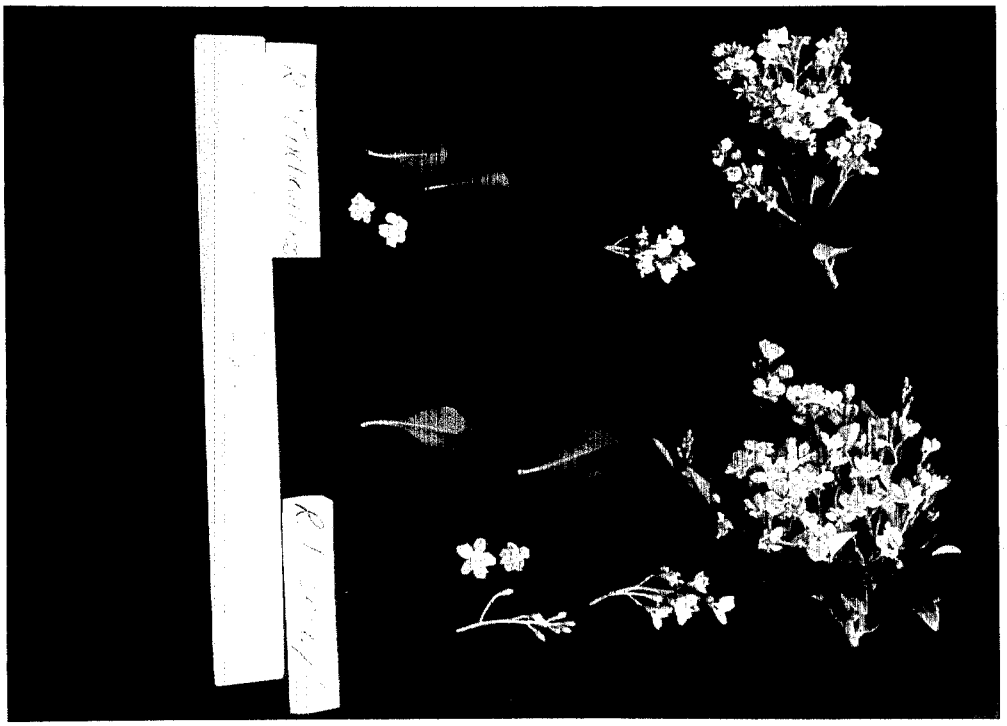

UNITED STATES PATENT AND TRADEMARK OFFICE

CERTIFICATE OF CORRECTION

PATENT NO. : Plant Pat. 05,215

DATED : April 3, 1984

INVENTOR(S) : William B. Usrey

It is certified that error appears in the above-identified patent and that said Letters Patent is hereby corrected as shown below: Title page:

In the Abstract lines 6 and 7, Enchantress" each occurrence, should read -- Moness --.

Column 1, lines 6, 7 and 25, "Enchantress" each occurrence, should read -- Moness --.

Signed and Sealed this

Tenth Day of January, 1989

*Attest:*

DONALD J. QUIGG

*Attesting Officer*

*Commissioner of Patents and Trademarks*